US00PP27756P2

(12) United States Plant Patent
Bradford

(10) Patent No.: US PP27,756 P2
(45) Date of Patent: Mar. 7, 2017

(54) ***FUCHSIA* PLANT NAMED 'FWULR24-0'**

(50) Latin Name: ***Fuchsia* hybrid**
Varietal Denomination: FWULR24-0

(71) Applicant: Marie Bradford, Foxley (GB)

(72) Inventor: Marie Bradford, Foxley (GB)

(73) Assignee: Floranova, Ltd. (GB)

( * ) Notice: Subject to any disclaimer, the term of this patent is extended or adjusted under 35 U.S.C. 154(b) by 25 days.

(21) Appl. No.: 14/756,097

(22) Filed: Aug. 3, 2015

(51) Int. Cl.
*A01H 5/02* (2006.01)

(52) U.S. Cl.
USPC ..... Plt./300

(58) Field of Classification Search
USPC ..... Plt./300
See application file for complete search history.

*Primary Examiner* — Keith Robinson
(74) *Attorney, Agent, or Firm* — Cassandra Bright

(57) ABSTRACT

A new and distinct *Fuchsia* cultivar named 'FWULR24-0' is disclosed, characterized by a strong, upright plant habit, with flowers occurring across the top of the plant. Plants are well branched, with strong stems and uniquely thick petals and calyx. The new variety is a *Fuchsia*, typically produced as a garden or container plant.

2 Drawing Sheets

Latin name of the genus and species: *Fuchsia* hybrid.
Variety denomination: 'FWULR24-0'.

BACKGROUND OF THE INVENTION

The new cultivar is a product of a planned breeding program. The new variety originated from a cross pollination of the seed parent, an unnamed, unpatented proprietary selection of *Fuchsia* hybrid with the pollen parent a different unnamed, unpatented *Fuchsia* hybrid. The crossing was made during the Summer of 2010, at a research greenhouse in Norfolk, UK. 'FWULR24-0' was discovered by the inventor, Marie Bradford at the same research greenhouse in May 2011.

Asexual reproduction of the new cultivar 'FWULR24-0' was first performed in Norfolk, UK, at a commercial greenhouse by vegetative terminal cuttings in Summer of 2011. 'FWULR24-0' has since produced several generations and has shown that the unique features of this cultivar are stable and reproduced true to type.

SUMMARY OF THE INVENTION

The cultivar 'FWULR24-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWULR24-0.' These characteristics in combination distinguish 'FWULR24-0' as a new and distinct *Fuchsia* cultivar:

1. Strong, upright growth habit.
2. Strong plant stems.
3. Well branched plants
4. Flowers occurring across the top of the plant.
5. Thick petals and calyx.

BRIEF DESCRIPTION OF THE PHOTOGRAPHS

Figure 1:
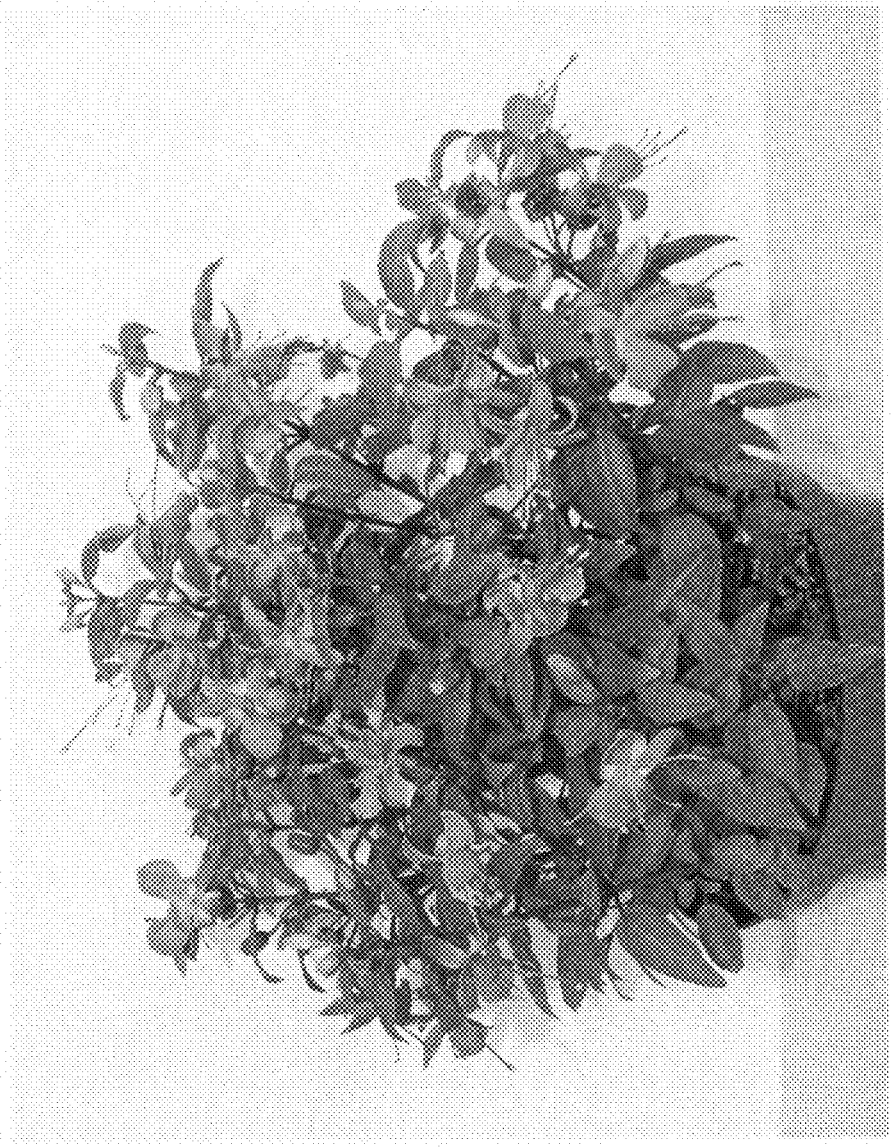

The accompanying photograph in FIG. 1 illustrates in full color a typical plant of 'FWULR24-0' grown outdoors in Santa Paula, Calif. This plant is approximately 30 weeks old, shown in a 1 gallon pot.

Figure 2:
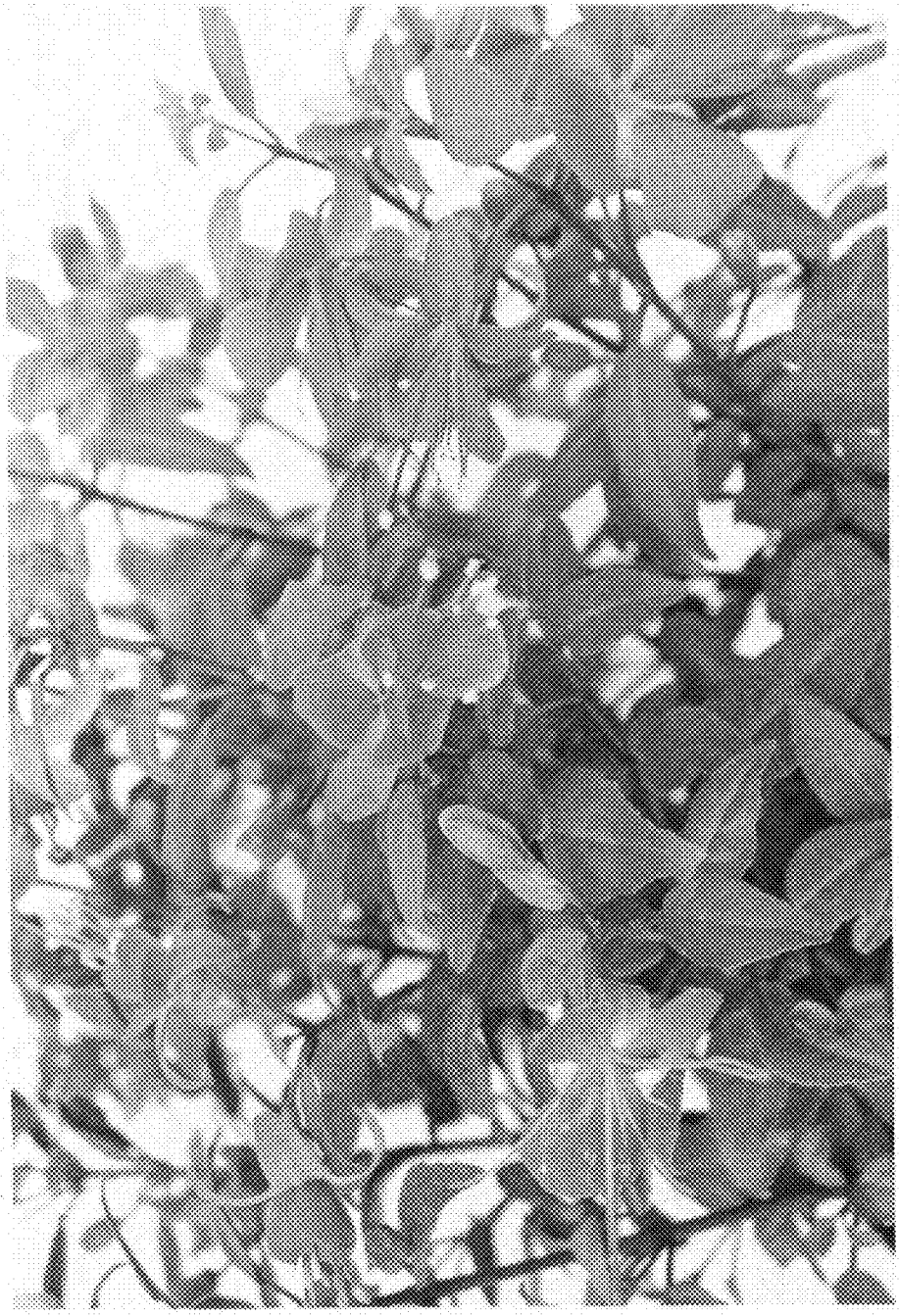

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'FWULR24-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWULR24-0'.

PROPAGATION

Propagation method: Vegetative Cuttings.
Time to initiate roots: About 2 weeks at 15° C. to 22° C.
Root description: Fine, densely fibrous.

PLANT

Age of plant described: Approximately 17 weeks from 3 rooted cuttings.
Pot size of plant described: 8 inch commercial pot.
Height: Approximately 33 cm from soil line of pot to top of foliar and uppermost flowering plane.

Plant spread: Approximately 28 cm.
Growth rate: Rapid.
Growth habit: Upright.
Branching characteristics: Moderately free branching.
Length of primary lateral branches: Average 11 to 18 cm.
Diameter of lateral branches: Approximately 0.5 cm.
Quantity of primary lateral branches: Approximately 15.
Characteristics of primary lateral branches:
*Color*.—Near RHS Greyed-Purple N186D.
*Texture*.—Glabrous.
*Strength*.—Strong, flexible.
Internode length: Average range 1.8 cm to 3.5 cm.

FOLIAGE

Leaf:
*Arrangement*.—Opposite.
*Quantity*.—Approximately 8 to 16 fully expanded leaves per primary lateral branch.
*Average length*.—6.3 cm, including petiole.
*Average width*.—2.5 cm.
*Shape of blade*.—Lanceolate.
*Apex*.—Acute.
*Base*.—Oblique.
*Margin*.—Infrequently dentate.
*Texture of top surface*.—Glabrous.
*Texture of bottom surface*.—Glabrous.
*Aspect*.—Mostly flat.
*Color*.—Young foliage upper side: Near RHS Green 138A. Young foliage under side: Near RHS Green 138B. Mature foliage upper side: Near RHS Green 137A. Mature foliage under side: Near RHS Green N138B.
*Venation*.—Type: Pinnate. Venation color upper side: Main vein near RHS Greyed-Purple 187B, lateral veins near Green 137A. Venation color under side: Main vein near RHS Greyed-Purple N186D, lateral veins near Green 137A. Attachment: Stalked.
*Petiole*.—Length: Average 1.1 cm. Diameter: Average 0.3 cm. Texture: Glabrous. Color: Upper surface: Near RHS Greyed-Purple N186D. Lower surface: Near RHS Greyed-Purple N186D.

FLOWER

Inflorescence and flower type and habit: 1 to 2 flowers emerge singly from each axil. Flowers emerge at different times, resulting in flowers of different maturity at each axil. Flowers are symmetrical and composed of a corolla surrounded by a decorative fused calyx. Flowers face outwardly.
Flowers per plant: Approximately 50 fully open flower and 30 buds on a mature plant.
Flower longevity on plant: Approximately 1 week for individual flowers.
Persistent or self-cleaning: Self-cleaning.
Flower size (petals and sepals only, not including protruding stamen and style):
*Length*.—Approximately 3.0 cm.
*Width*.—Approximately 2.8 cm.
Bud:
*Shape*.—Oblong.
*Length*.—2.1 cm.
*Diameter*.—1.1 cm.
*Color*.—Near RHS Red 54B.
Corolla:
Petals (measured from separation at top of tube):
*Number*.—Average 5 to 7.
*Length*.—Approximately 1.6 cm.
*Width*.—Approximately 1.4 cm.
*Shape*.—Orbicular.
*Aspect*.—Somewhat cupped or slightly undulating.
*Margin*.—Entire.
*Texture*.—Glabrous, all surfaces.
*Appearance*.—Matte.
*Apex*.—Obtuse.
*Color*.—When opening: Upper surface: Near RHS Purple 77B, main vein near Red-Purple N74B. Lower surface: Near RHS Purple 77A, main vein near Red-Purple N74A. Fully opened: Upper surface: Near RHS Red-Purple 72B. Lower surface: Near RHS Red-Purple 72A. Fading: Upper surface: Near RHS Red-Purple 72C. Lower surface: Near RHS Red-Purple 72B.
Calyx:
*Form*.—Funnelform base, separating approximately 25% from base, to flaring out into 4 large decorative deltoid shaped sepals. Sepals reflexed back.
*Fused section*.—Length: Approximately 0.9 cm. Diameter: Approximately 0.7 cm.
*Unfused section*.—Length: Approximately 2.3 cm. Diameter: Approximately 0.85 cm.
*Sepal texture*.—Glabrous all surfaces.
*Appearance*.—Bright and vibrant, somewhat iridescent.
*Apex*.—Acute.
*Color*.—Upper Surface: Near RHS Red-Purple 57C, but brighter. Lower Surface: Near RHS Red-Purple 62C, flushed along margin 57C.
*Fragrance*.—None.
Peduncle:
*Length*.—Average 1.4 cm.
*Diameter*.—0.2 cm.
*Color*.—Near RHS Greyed-Purple 183B.
*Texture*.—Glabrous.

REPRODUCTIVE ORGANS

Stamens:
*Number (per flower)*.—Typically 8.
*Filament length*.—Average 2.3 cm.
*Filament color*.—Near RHS Red-Purple 58B.
*Anthers*.—Shape: Globular. Length: Approximately 0.1 cm. Color: Near RHS Red-Purple 170A.
*Pollen*.—Amount: Scarce, colored Orange-White 159C.
Pistils:
*Quantity per flower*.—1.
*Length*.—Approximately 4.5 cm.
*Style*.—Length: Approximately 4.0 cm. Color: Base near RHS Red-Purple N66C, upper ⅔ near Red-Purple 71A.
*Stigma*.—Shape: Globular. Color: Near Greyed-Red 180D. Ovary: Length: Approximately 0.5 cm. Diameter: Approximately 0.4 cm. Color: Near RHS Green 143B.

OTHER CHARACTERISTICS

Seeds and fruits: Not observed to date.

Disease/pest resistance: Neither resistance nor susceptibility to normal diseases and pests of *Fuchsia* has been observed.

Temperature tolerance: Tolerates temperatures from approximately −1° C. to 38° C.

Drought tolerance: No tolerance for drought.

What is claimed is:

1. A new and distinct cultivar of *Fuchsia* plant named 'FWULR24-0' as herein illustrated and described.

* * * * *